US012370325B2

(12) United States Patent
Chopra

(10) Patent No.: US 12,370,325 B2
(45) Date of Patent: *Jul. 29, 2025

(54) NEEDLE WITH MULTI-BEVEL TIP GEOMETRY

(71) Applicant: FACET TECHNOLOGIES, LLC, Atlanta, GA (US)

(72) Inventor: Benjamin Chopra, Atlanta, GA (US)

(73) Assignee: FACET TECHNOLOGIES, LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/471,057

(22) Filed: Sep. 20, 2023

(65) Prior Publication Data

US 2024/0042139 A1 Feb. 8, 2024

Related U.S. Application Data

(63) Continuation of application No. 15/533,830, filed as application No. PCT/US2015/064923 on Dec. 10, 2015, now Pat. No. 11,793,942.

(60) Provisional application No. 62/150,697, filed on Apr. 21, 2015, provisional application No. 62/090,548, filed on Dec. 11, 2014.

(51) Int. Cl.
*A61M 5/32* (2006.01)

(52) U.S. Cl.
CPC .......... *A61M 5/3286* (2013.01); *A61M 5/329* (2013.01); *A61M 2205/195* (2013.01)

(58) Field of Classification Search
CPC .................. A61M 5/3286; A61M 2205/195
See application file for complete search history.

(56) References Cited

U.S. PATENT DOCUMENTS 11,793,942 B2 * 10/2023 Chopra ............... A61M 5/3286

* cited by examiner

*Primary Examiner* — James D Ponton
*Assistant Examiner* — Hong-Van N Trinh
(74) *Attorney, Agent, or Firm* — Perilla Knox & Hildebrandt LLP; Bradley K. Groff; Stephanie L. Davy-Jow

(57) ABSTRACT

A multi-beveled needle point geometry for hypodermic needles such as pen needles. A proximal bevel is formed at a first angle of inclination, a pair of intermediate bevels at a second angle of inclination, and a pair of distal bevels at a third angle of inclination and differing angles of rotation. The second angle of inclination is substantially different than the first angle of inclination to define a marked apex at the intersections between the proximal bevel and the intermediate bevels. At least one smooth transition is typically provided between adjacent bevels, between a bevel and an outer surface of the needle, and/or between a bevel and the lumen of the needle.

14 Claims, 17 Drawing Sheets

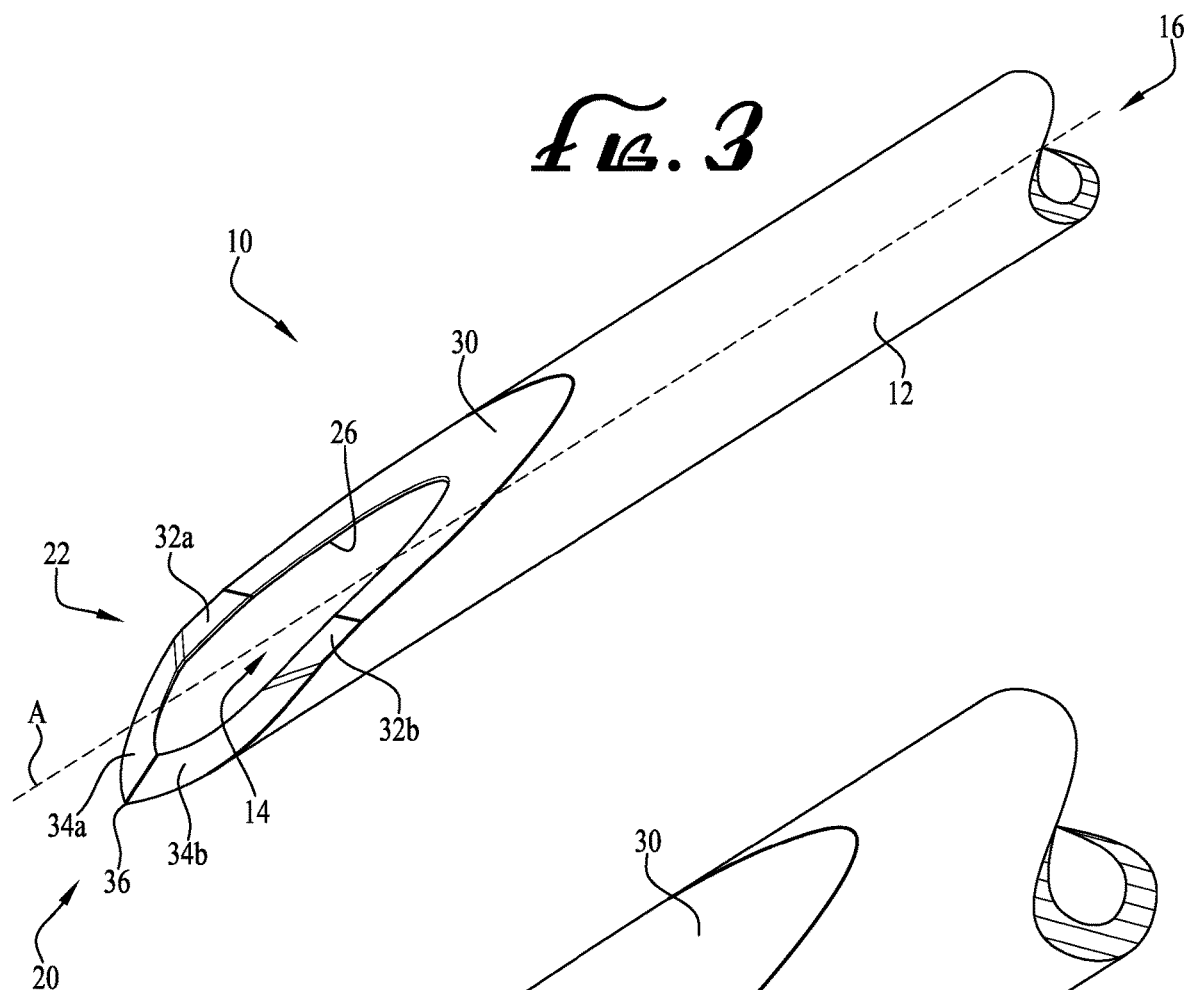
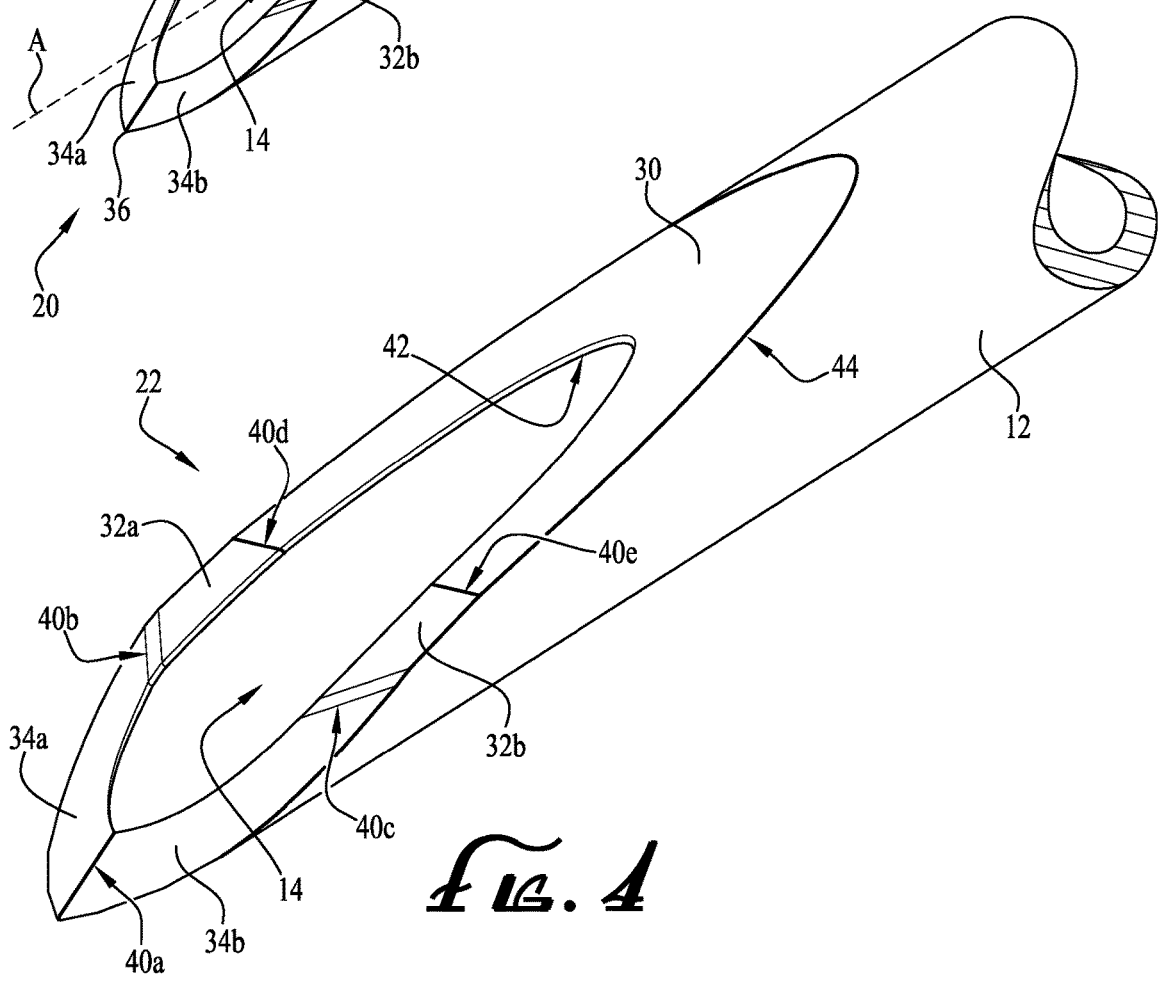

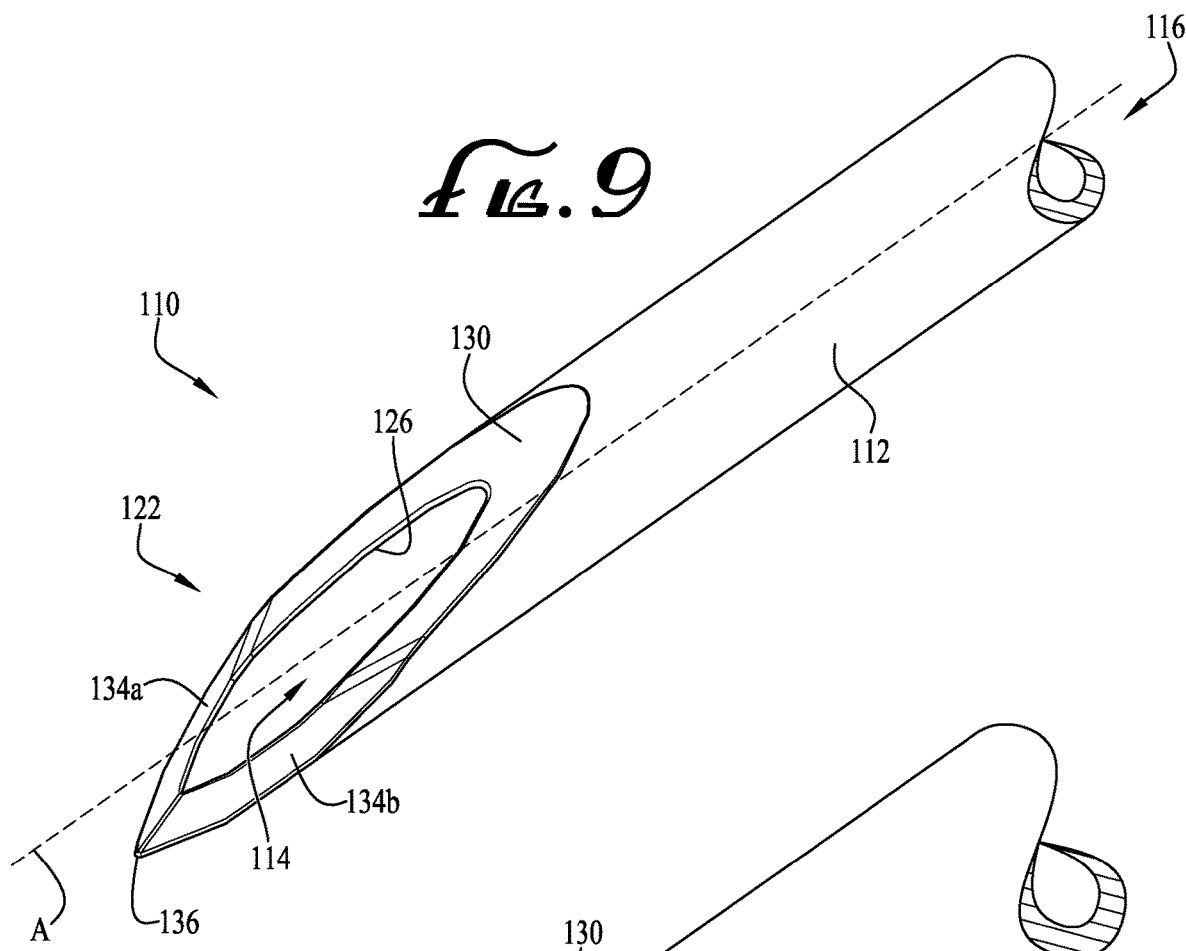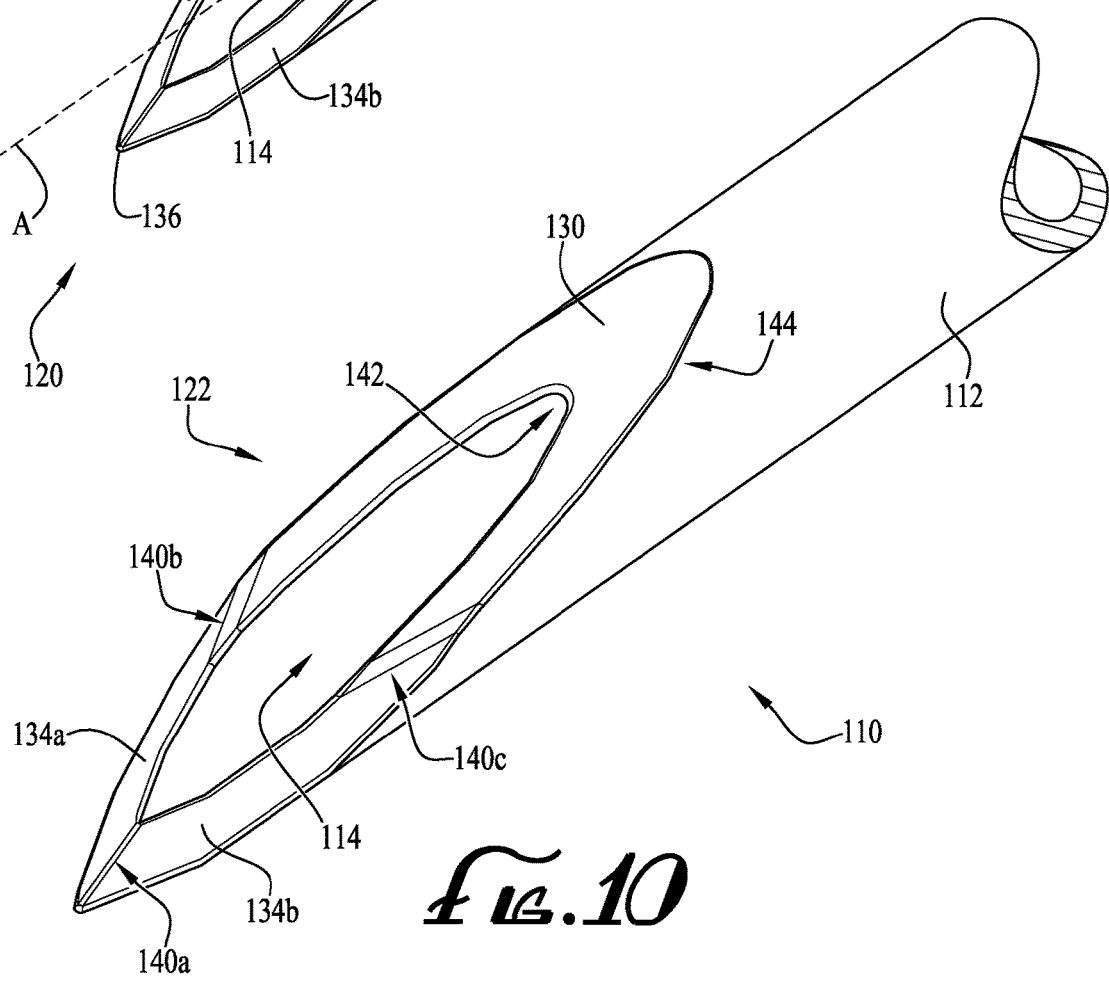

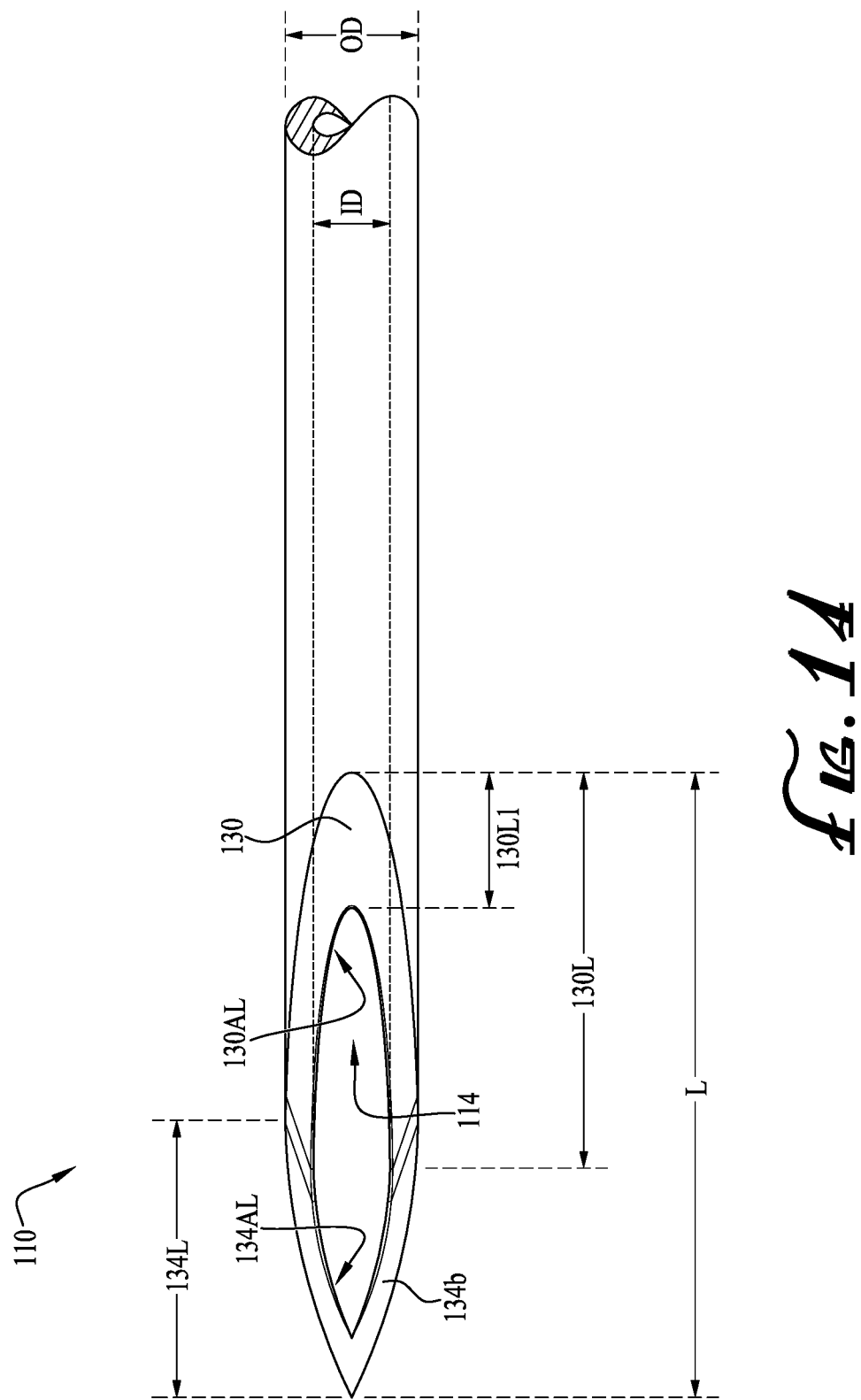

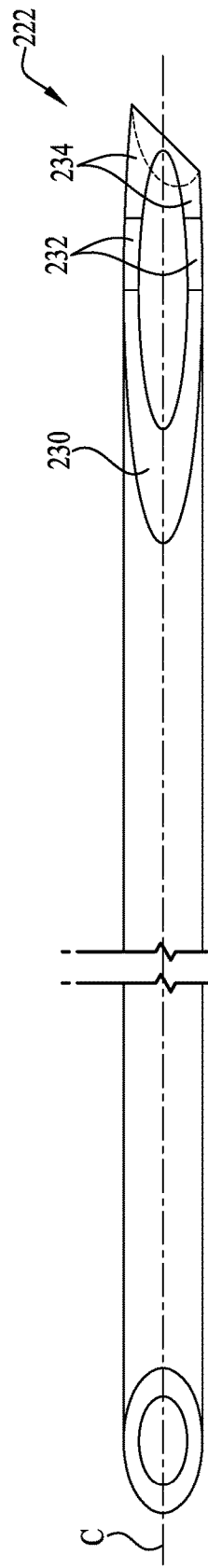
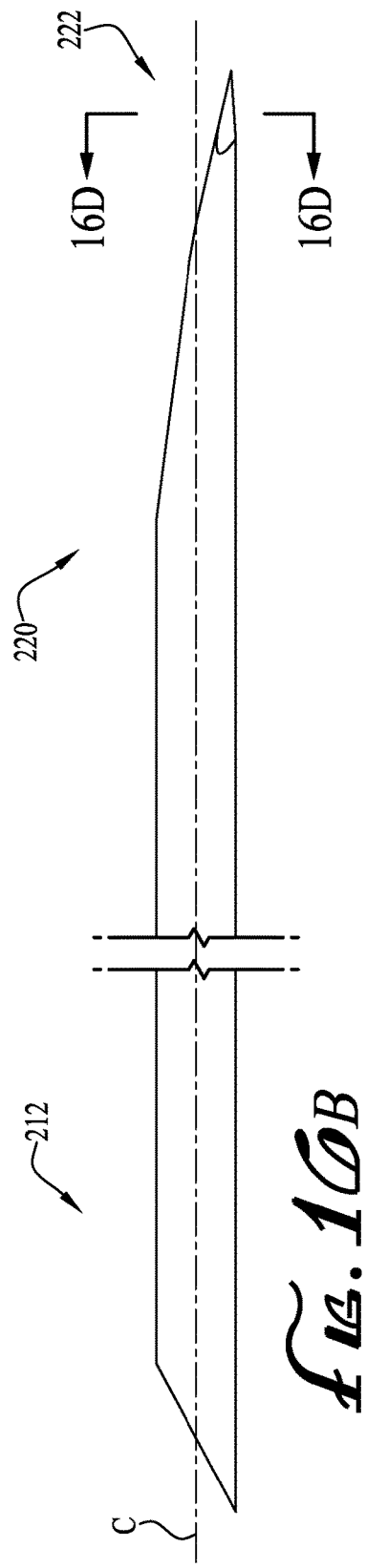
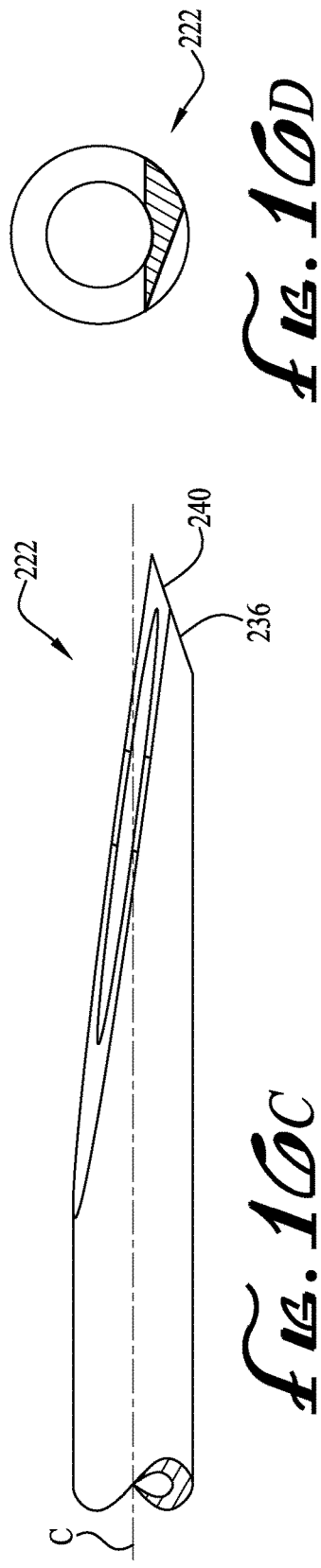
Fig. 16A
Fig. 16B
Fig. 16C
Fig. 16D

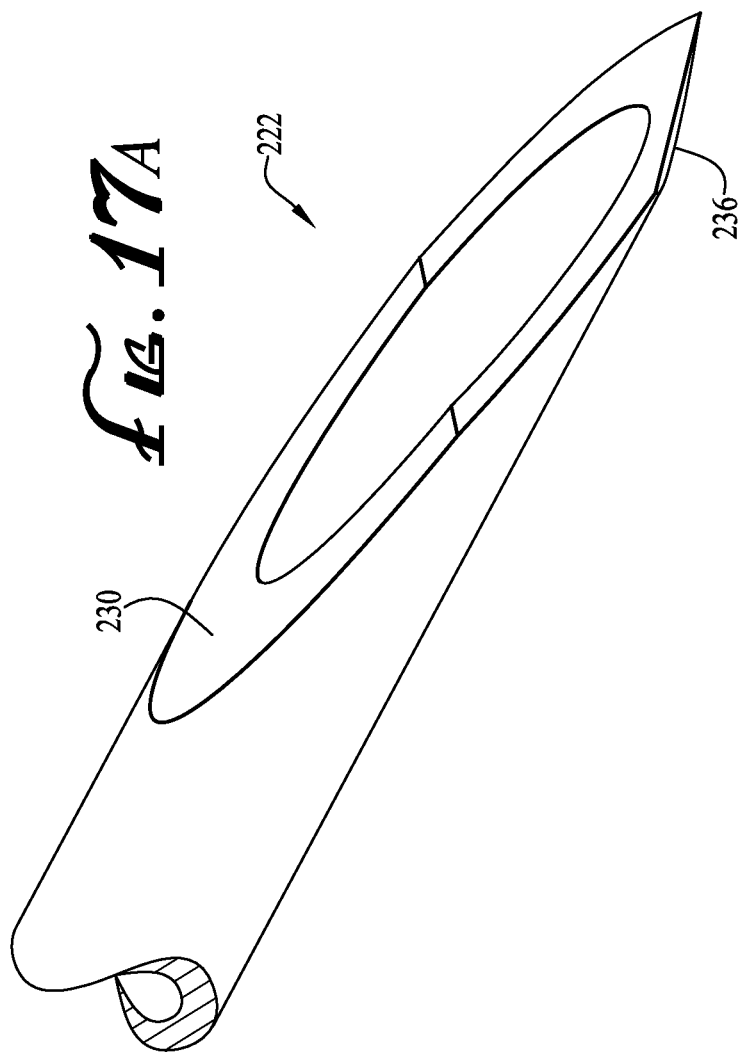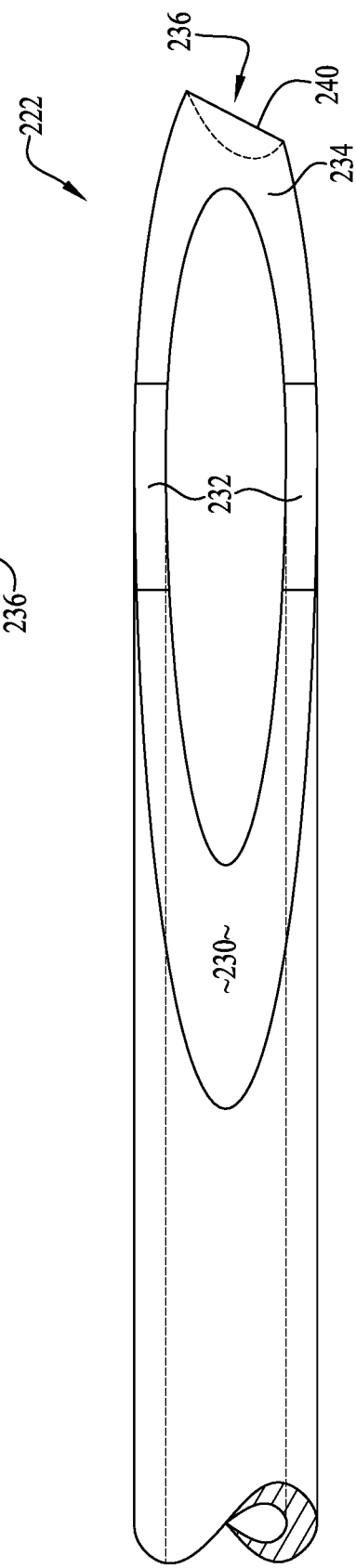

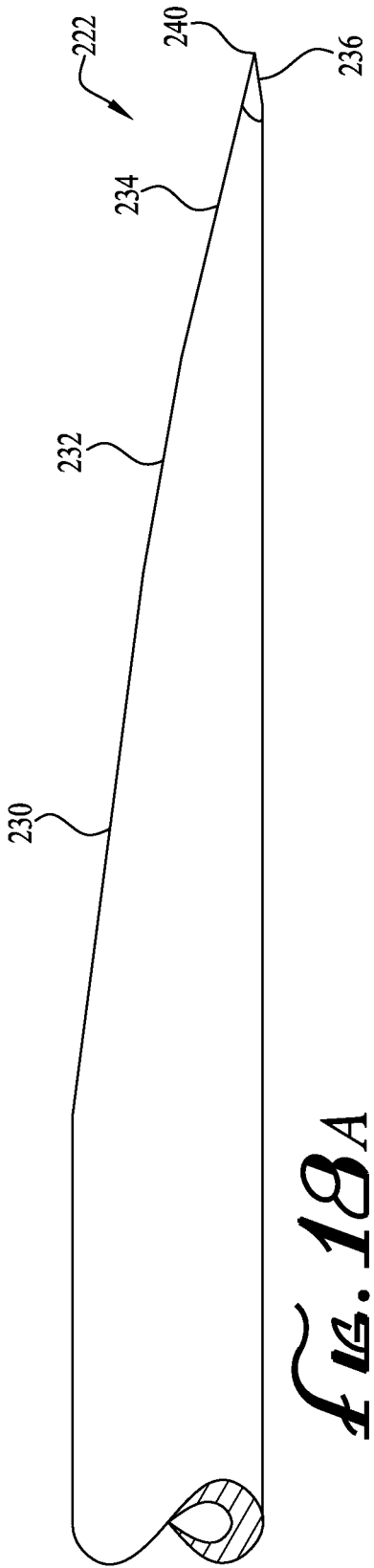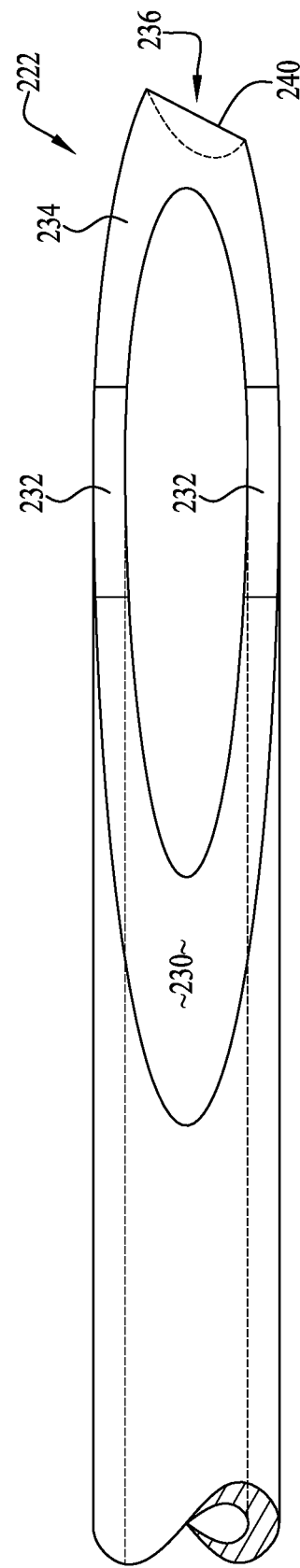

NEEDLE WITH MULTI-BEVEL TIP GEOMETRY

CROSS-REFERENCE TO RELATED APPLICATIONS

This application is a continuation of U.S. patent application Ser. No. 15/533,830, which is a National Phase of PCT Patent Application No. PCT/US2015/064923 filed Dec. 10, 2015, which claims the benefit of U.S. Provisional Patent Application Ser. No. 62/090,548 filed Dec. 11, 2014, and of U.S. Provisional Patent Application Ser. No. 62/150,697 filed Apr. 21, 2015, the entireties of which are hereby incorporated herein by reference for all purposes.

TECHNICAL FIELD

The present invention relates generally to the field of hypodermic needles for medical use, and more particularly to improved tip geometries for needles such as for example pen needles used with injection pens for delivery of insulin or other medications.

BACKGROUND

Various forms of hypodermic needles are used for the delivery of injectable medications into the body through the skin of a human or animal patient, for sampling of blood, and for other medical and research purposes. Pen needles, for example, are commonly used by healthcare providers and patients for delivery of medications such as insulin for diabetes management.

Pen needles typically include a plastic hub with a hollow needle embedded therein. One end of the needle has a sharp tip for injection through the skin of the patient, and the other end is configured to receive medication delivered by an injection pen. The hub of the pen needle typically includes threaded or snap connections for removable attachment to the injection pen, so that the needle can be removed after use and replaced with a new needle for subsequent use of the injection pen.

The sharp injection point or tip geometry of a hypodermic needle may affect its function and/or play a part in user preferences. For example, different tip geometries may require more or less force to penetrate the skin during an injection, and/or different users may perceive different pain levels or different tactile feedback resulting from injections with needles having different tip geometries.

SUMMARY

The present invention relates to improved tip geometries for hypodermic needles or cannulas used, for example, in the delivery of medication, in blood sampling, or in other medical or research applications. In example forms, the invention relates to improved tip geometries for pen needles used in combination with injection pens, such as for example in the administration of insulin for diabetes management.

In one aspect, the present invention relates to a multi-beveled needle tip geometry having a proximal bevel formed at a first angle of inclination relative to the longitudinal axis of the needle shaft, a pair of intermediate bevels formed at a different second angle of inclination relative to the longitudinal axis, and a pair of distal bevels formed at a third angle of inclination relative to the longitudinal axis and/or at different angles of rotation relative to the longitudinal axis of the needle shaft and/or relative to a vertical axis generally transverse and orthogonal to the longitudinal axis of the needle. Preferably, no rotational offset is provided between the proximal bevel and the intermediate bevels, and the substantially different first and second angles of inclination define a marked apex or peak at the intersection of the proximal bevel with each of the intermediate bevels.

Optionally, one or more radiused transitions are formed at the intersection of adjacent bevels to provide a smoother transition between angular offsets between the bevels, between at least one of the bevels and the lumen of the needle, and/or between at least one of the bevels and an outer surface of the needle.

In another aspect, the invention relates to a multi-beveled pen needle including a needle shaft or cannula and a multi-beveled point. Preferably, at least one radiused transition is formed between adjacent bevels, between at least one of the bevels and the lumen, and/or between at least one of the bevels and an outer surface of the cannula such that a clear transition or intersection forming an edge or discontinuity between adjacent surface features is not present.

In still another aspect, the invention relates to a method of forming a multi-beveled pen needle tip including: providing a hollow needle or cannula extending from a proximal end to a distal end along a longitudinal axis, the needle comprising a lumen extending therethrough along the longitudinal axis; affixing the proximal end of the needle within a fixture, the distal end being generally free from engagement therewith; positioning the needle at a first inclination angle relative to the longitudinal axis; grinding the distal end to form a proximal bevel; positioning the needle at a second inclination angle relative to the longitudinal axis; grinding the distal end to form a pair of intermediate bevels, the intermediate bevels being generally adjacent the proximal bevel; positioning the needle at a third inclination angle relative to the longitudinal axis; rotating the needle about the longitudinal axis to a first rotational angle relative to a vertical axis, the vertical axis being generally transverse relative to the longitudinal axis; grinding the distal end to form a first distal bevel; rotating the needle about the longitudinal axis to a second rotational angle relative to the vertical axis, the second rotational angle being generally opposite the first rotational angle; grinding the distal end to form a second distal bevel; and forming a smooth and radiused transition between at least two of the bevels, between at least one of the bevels and the lumen, and between at least one of the bevels and an outer surface of the needle.

In yet another aspect, the invention relates to a multi-beveled pen needle including a multi-beveled point and at least one smoothed and radiused transition between adjacent bevels, between at least one of the bevels and the lumen, and/or between at least one of the bevels and an outer surface of the needle. The needle generally extends from a proximal end to a distal end along a longitudinal axis and includes an elongate lumen extending therethrough. The multi-beveled point is formed proximal at least one of the ends of the needle and includes at least a proximal bevel and a pair of distal bevels. The proximal bevel is formed at a first angle of inclination relative to the longitudinal axis and the pair of distal bevels are formed generally symmetrically at both a second angle of inclination and corresponding angles of rotation relative to the longitudinal axis and/or a vertical axis positioned transverse to the longitudinal axis. The different first and second angles of inclination result in an apex or peak at bevel intersections, which optionally may be rounded or radiused to provide a smoother transition between bevels.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of example embodiments are explanatory of example embodiments of the invention, and are not restrictive of the invention, as claimed.

BRIEF DESCRIPTION OF THE DRAWINGS

FIG. 3 is a perspective view of a needle-tip portion of the pen needle of FIG. 1, showing a needle-tip geometry according to an example embodiment of the invention.

FIG. 4 is a detailed view of the needle-tip portion of FIG. 3, showing smooth radiused transitions between the bevels, between the bevels and the interior surface of the lumen, and between the bevels and the outer periphery of the needle.

FIG. 9 is a perspective view of a needle tip according to another example embodiment of the present invention.

FIG. 10 is a perspective view of the needle-tip portion of FIG. 9, showing smooth radiused transitions between the bevels, between the bevels and the interior surface of the lumen, and between the bevels and the outer periphery of the needle.

FIG. 14 is a top view of the needle-tip portion of FIG. 9.

FIGS. 16A-16D show top, side, side perspective and end views, respectively, of a needle, for example for use in a pen needle assembly according to FIG. 15A, having a multi-bevel needle tip geometry according to a further example embodiment of the invention.

FIGS. 17A and 17B show detailed perspective and top views of a needle having a multi-bevel needle tip geometry according to an example embodiment of the invention.

FIGS. 18A and 18B show detailed side and top views of a needle having a multi-bevel needle tip geometry according to an example embodiment of the invention.

DETAILED DESCRIPTION OF EXAMPLE EMBODIMENTS

The present invention may be understood more readily by reference to the following detailed description of example embodiments in conjunction with the accompanying drawing figures, which form a part of this disclosure. It is to be understood that this invention is not limited to the specific devices, methods, conditions, or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
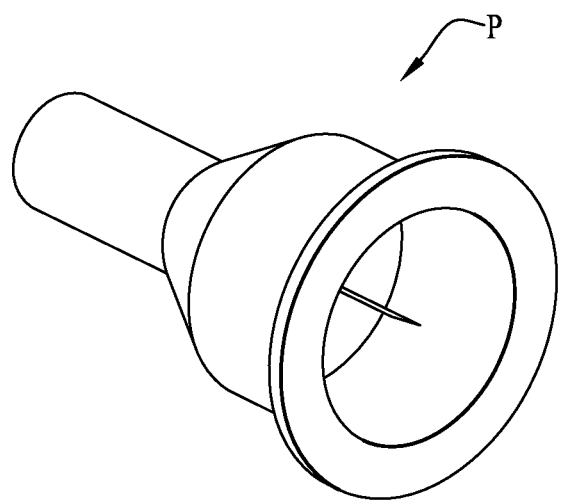
FIG. 1 is a distal-end perspective view of a pen needle according to an example embodiment of the present invention.
Figure 2:
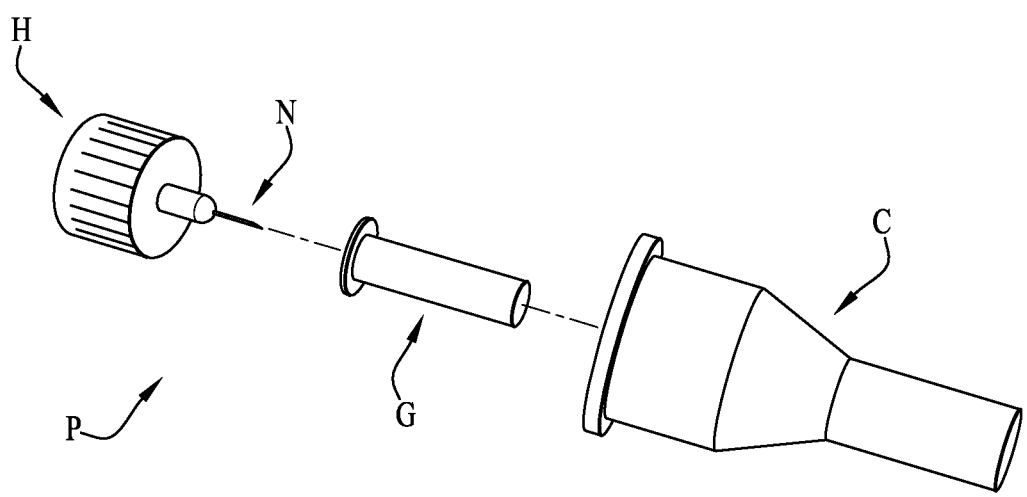
FIG. 2 is a perspective assembly view of the pen needle of FIG. 1, shown with the protective caps or covers separated from the needle hub and with the sharp tip of the needle exposed.

With reference now to the drawing figures, wherein like reference numbers represent corresponding parts throughout the several views, FIG. 1 shows a pen needle P in example form. FIG. 2 shows the pen needle P, with its needle guard G and cover C removed from the hub H, to expose the sharp needle tip N. In some example forms, the needle guard G and/or the cover C are/is color tinted.

FIGS. 3-8 show a sharp point or tip geometry of a needle 10 according to an example embodiment of the present invention. In example forms, the needle 10 can comprise the needle N of a pen needle P such as is shown in FIGS. 1 and 2, the needle of a standard hypodermic syringe, or the needle of various other devices for injection or other medical or research applications. The needle 10 generally comprises a tube or cannula 12 defining a fluid-carrying duct or lumen 14 extending therethrough along a longitudinal axis A from a proximal end 16 to a distal end 20. In typical embodiments, both the cannula 12 and the lumen 14 (i.e., the inner and outer wall surfaces of the cannula) are generally cylindrical in shape and concentrically or coaxially positioned relative to each other to generally define a substantially continuous wall thickness along the length of the cannula 12. The proximal end 16 and/or medial portions of the needle 10 are configured for attachment to the hub of a pen needle, to the barrel of a syringe assembly, or to another device or fixture.

The distal end 20 preferably comprises a multi-beveled point 22 including a plurality of beveled faces, for example as detailed herein. While generally described herein with respect to embodiments taking the form of a pen needle tip geometry, the tip geometry of the present invention may also be adapted to use in connection with various other items, such as for example hypodermic needles, lancets, catheters and the like.

The multi-beveled point 22 is generally characterized by an axial length L (see FIG. 8), and the plurality of beveled faces thereof are generally formed around/along a periphery 26 of the lumen 14. The plurality of bevels may contiguously bound the distal opening of the lumen 14 or may be spaced a distance from the edge of the lumen. In the embodiment of FIGS. 3-8, the multi-beveled point 22 comprises a proximal bevel 30, a pair of intermediate bevels 32a, 32b, and a pair of distal bevels 34a, 34b. In the depicted embodiment, the pair of intermediate bevels 32a, 32b and the pair of distal bevels 34a, 34b are symmetrically formed relative to the proximal bevel 30, but in alternate embodiments the bevel configuration may be asymmetric.

Figure 5:
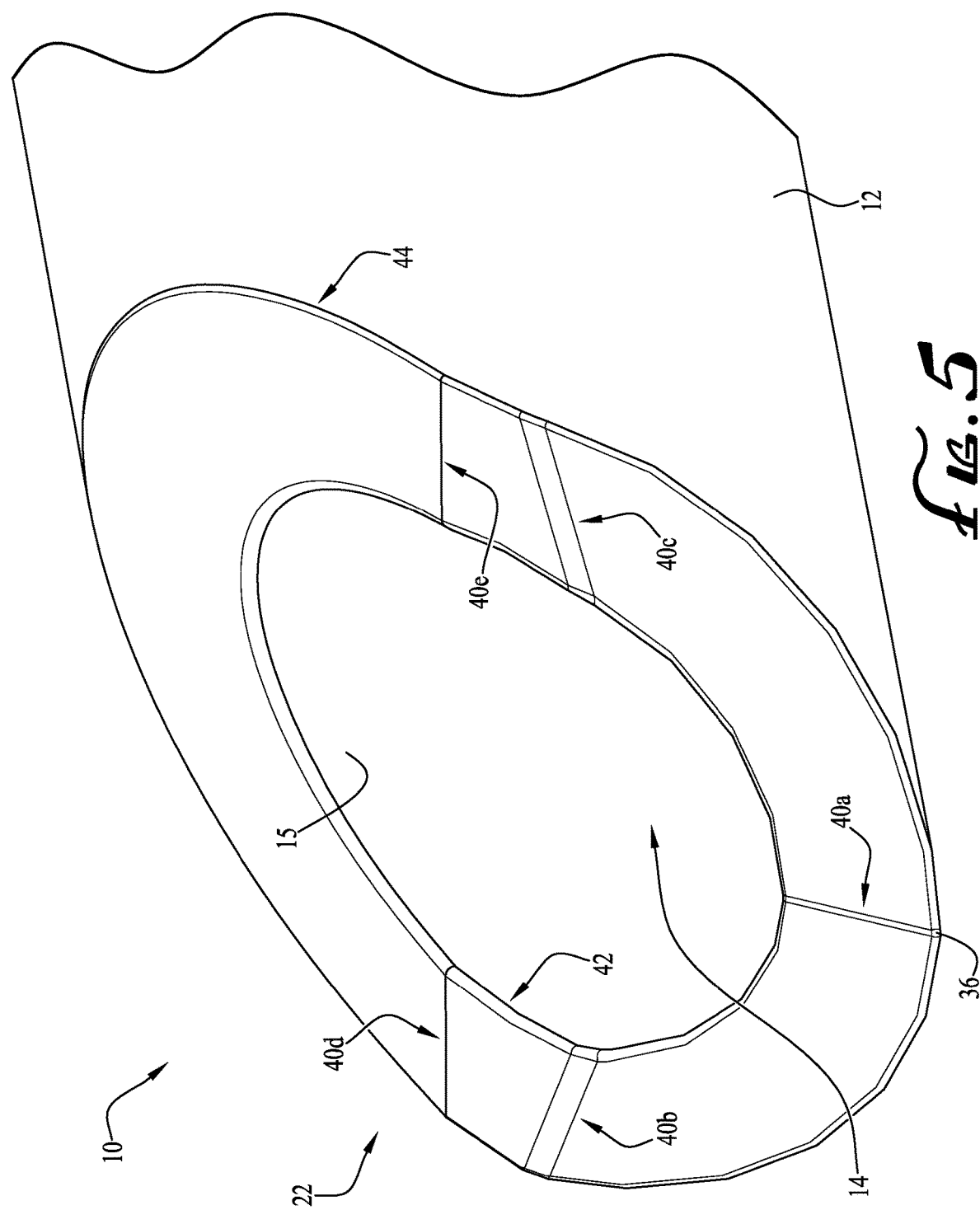
FIG. 5 is a further-detail and different-perspective view of the needle-tip portion of FIG. 3.
Figure 6:
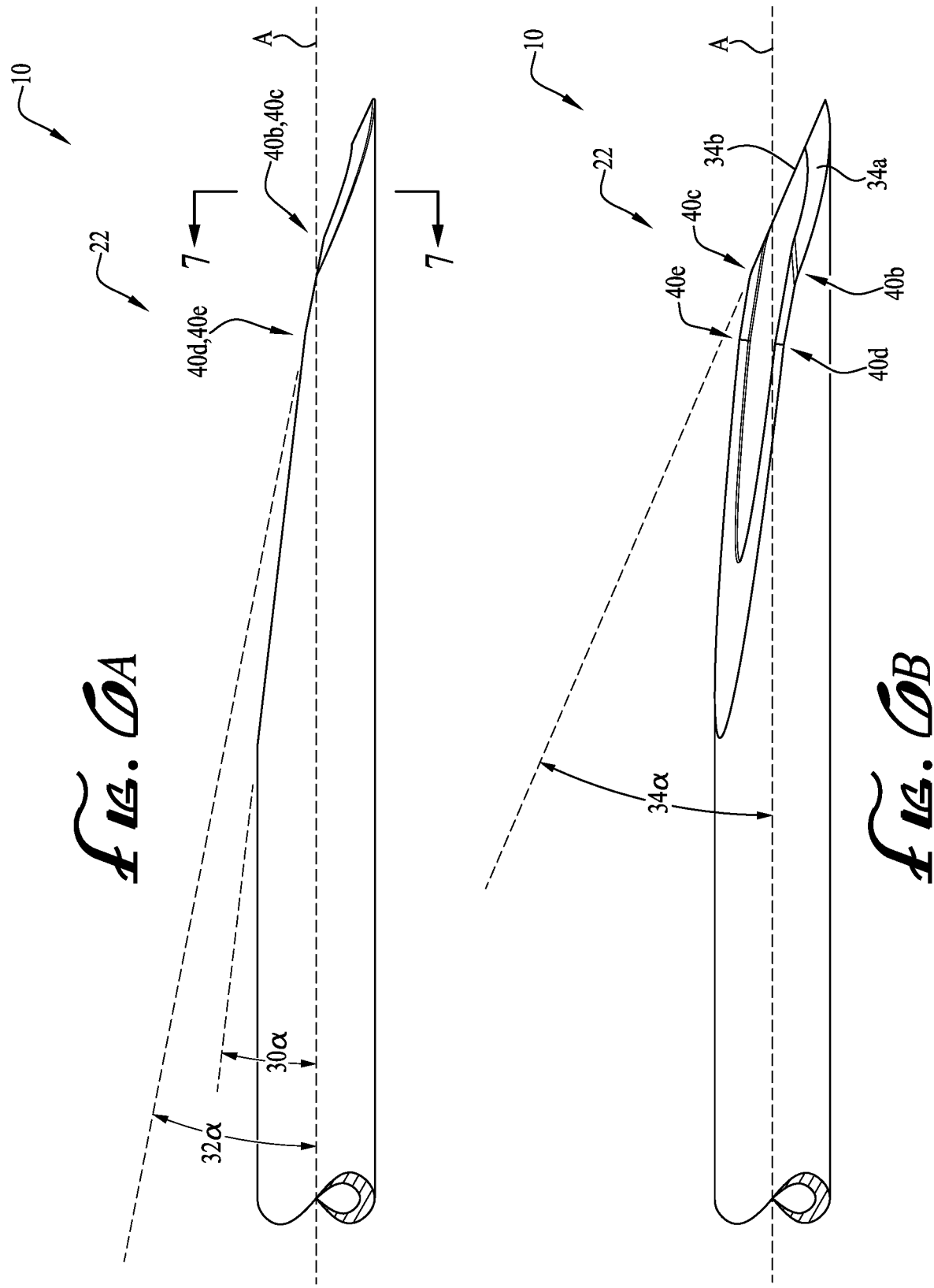
FIG. 6A is a side view of the needle-tip portion of FIG. 3, showing the inclination angles of the proximal and intermediate bevels.
FIG. 6B is a side perspective view of the needle-tip portion of FIG. 6A, showing the inclination angle of the distal bevels.

Optionally, a radiused, rounded, or otherwise smooth transition zone is formed between the bevels (generally axially), between the bevels and the lumen (generally radially), and/or between the bevels and the outer periphery of the cannula 12 (generally radially). For example, as depicted in FIGS. 4 and 5, a first smooth transition 40a is provided between the distal bevels 34a, 34b, meeting together at an longitudinal apex 36. A second smooth transition 40b is provided between the distal bevel 34a and the intermediate bevel 32a, a third smooth transition 40c is provided between the distal bevel 34b and the intermediate bevel 32b, a fourth smooth transition 40d is provided between the intermediate bevel 32a and a portion of the proximal bevel 30, and a fifth smooth transition 40e is provided between the intermediate bevel 32b and a portion of the proximal bevel 30. In example embodiments, a smooth transition 42 is also provided between each of the bevels positioned along the periphery 26 of the lumen 14 and an interior surface 15 of the lumen 14 (e.g., bevel-to-intralumen transition), and a smooth transition 44 is provided between the intersection of each of the bevels and the outer surface or periphery of the cannula 12. In example forms, the smooth transitions generally comprise a radius of curvature R of between about R 0.0001-R 0.035 millimeters, for example about R 0.02 millimeters. Preferably, the smooth transitions avoid a sharp edge or clearly defined intersection between the bevels and other surfaces of the needle tip such that transitions between the surfaces are smooth. The smooth transitions may be formed, for example, by bead blasting, grinding, polishing, coating or otherwise treating the needle surface(s).

Figure 7:
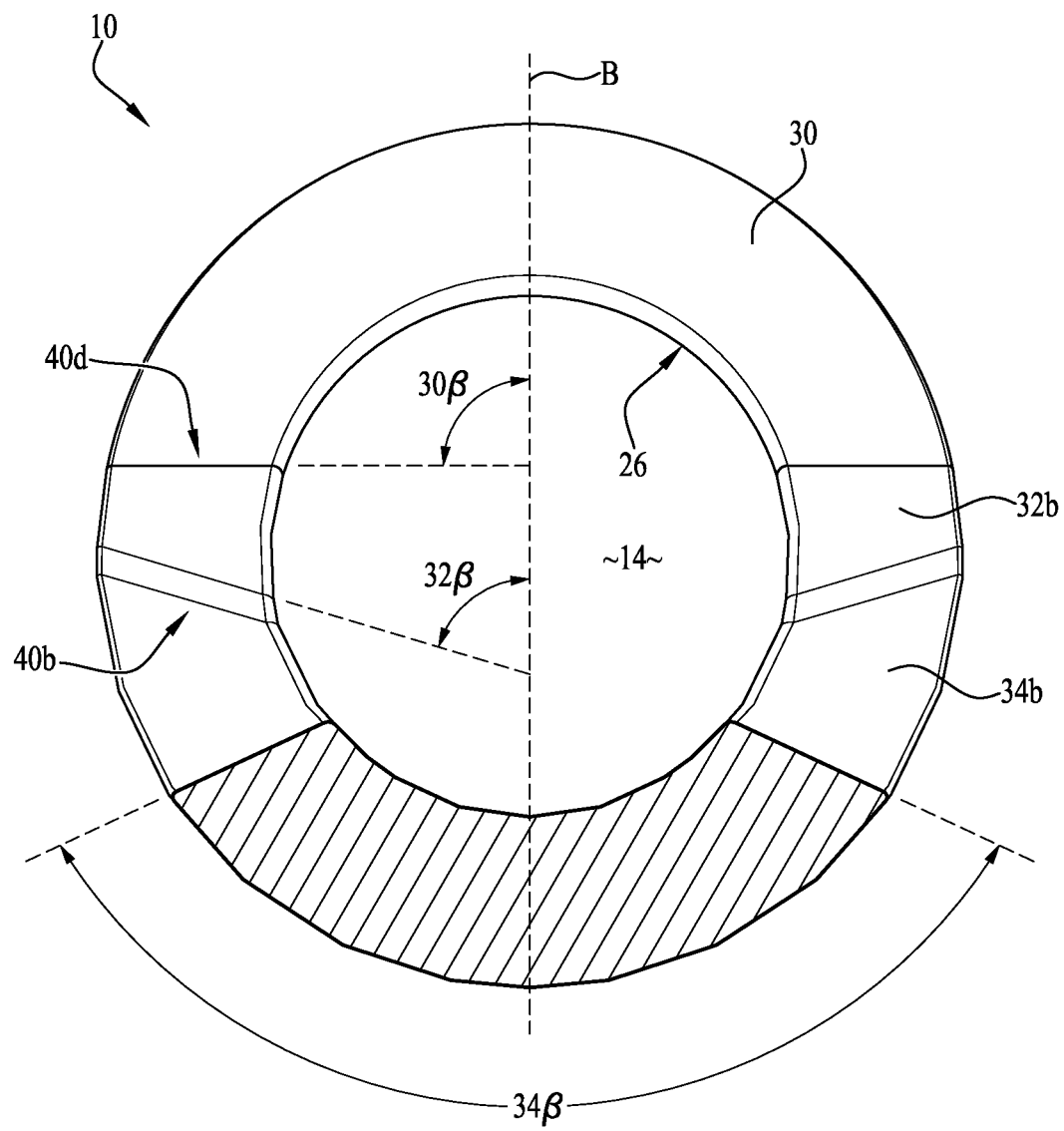
FIG. 7 is a partial cross-sectional view of the needle-tip portion of FIG. 6A taken along line 7-7, showing the angle of rotation of the distal bevels.

FIGS. 6A, 6B and 7 show further details of the multi-bevel point 22. As depicted in FIG. 6A, the proximal bevel 30 is formed at a first inclination angle 30a and the intermediate bevels 32a, 32b are formed at a substantially different (i.e., not substantially equal) second inclination angle 32α, the angles 30α and 32α being defined relative to the longitudinal axis A of the needle shaft. The proximal and intermediate bevels 30, 32a-b are preferably formed at the same rotational angle (i.e., with no rotational offset about the longitudinal axis A). The first inclination angle 30a may be, for example, between about 7.3-7.7 degrees relative to the axis A, and the second inclination angle 32a may be, for example, between about 9.3-9.7 degrees relative to the axis A, thus defining an angular offset or difference of about 2 degrees (i.e., about 20%-25% relative difference in the angles 30α and 32α). In alternate embodiments, the first inclination angle 30α is, for example between about 6.0-9.0 degrees, and the second inclination angle 32a is, for example between about 8.0-11.0 degrees. In still other embodiments, the first inclination angle 32α is about 8 degrees and the second inclination angle 32α is about 10 degrees, resulting in a difference of about 2 degrees (i.e., about 22% different). Preferably, the angular offset or difference between the first inclination angle 30α and the second inclination angle 32α is at least about 1.0-2.0 degrees or more, or at least about a 10%-20% difference or more. Provision of substantially unequal first and second inclination angles 30α and 32α in this manner results in a marked apex or peak at the intersections of the proximal bevel 30 and the intermediate bevels 32a, 32b, in the vicinity of the rounded or smooth transitions 40d and 40e.

With reference to FIG. 6B, the distal bevels 34a, 34b are formed at a third inclination angle 34a relative to the longitudinal axis A, of for example between about 18-19 degrees. In alternate embodiments, the third inclination angle 34α is between about 17-20 degrees relative to the longitudinal axis A, or for example between about 22.2-22.3 degrees. Preferably, prior to forming the distal bevels 34a, 34b, the pen needle 10 is rotated about the longitudinal axis A in the clockwise and counterclockwise directions respectively, to form the distal bevels 34a, 34b at substantially different rotational angles (as well as at an inclination angle as described above) relative to the proximal and intermediate bevels 30, 32a, 32b. As depicted in FIG. 7, the entire rotation of the needle 10 between the first distal bevel 34a and the second distal bevel 34b (shown as rotation angle 34β) is about 130 degrees relative to a vertical axis B. Thus, to form the first distal bevel 34a, the needle is rotated about the longitudinal axis A in the clockwise direction a rotational angle of about 65 degrees and inclined at the inclination angle 34a. Similarly, to form the second distal bevel 34b, the needle 10 is rotated about the longitudinal axis A in the counterclockwise direction (from the 65 degrees clockwise position) about 130 degrees in the counterclockwise direction while remaining at the inclination angle 34α. Thus, in example forms, the rotational angle for forming the distal bevels 34a, 34b is generally provided by rotating the needle 10 about 65 degrees in both the clockwise and counterclockwise directions about the longitudinal axis A. Optionally, the rotational angles can be between about 55-75 degrees in the clockwise and counterclockwise directions.

The smooth transitions between the bevels may be configured such that an angle 30β is defined between the vertical axis B and the smooth transitions 40d, 40e, and an angle 32β is provided between the vertical axis B and the smooth transitions 40b, 40c. In example embodiments, the angle 30β is about 90 degrees and the angle 32β is about 73 degrees. Preferably, since the angle of rotation between the proximal bevel 30 and the intermediate bevels 32a, 32b is exactly (or at least substantially) zero, the angle 30β will generally remain close to 90 degrees. And, since the needle 10 is rotated in the clockwise and counterclockwise directions prior to forming the distal bevels 34a, 34b, the angle 32β will generally be between about 60 degrees to about 80 degrees relative to the vertical axis B.

Figure 8:
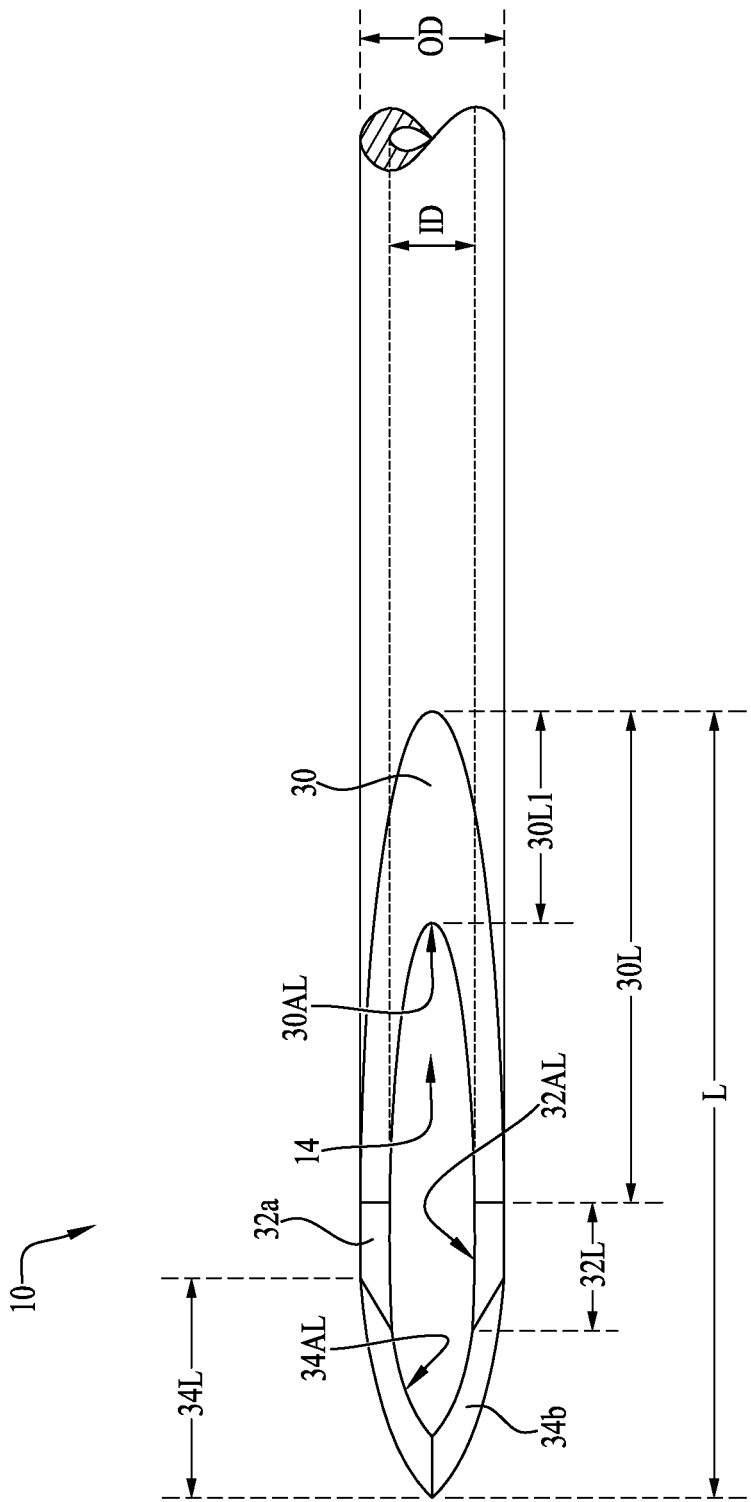
FIG. 8 is a top view of the needle-tip portion of FIG. 3.

With reference to FIG. 8, in example embodiments, the overall axial length L of the multi-beveled surface 22 is between about 1.3-1.45 millimeters. In further example embodiments, the length L is between about 1.32-1.42 millimeters. In further example embodiments, the length L is between about 1.20-1.60 millimeters. In example embodiments, the length 30L of the proximal bevel 30 is between about 0.800-0.900 millimeters, the length 32L of the intermediate bevels 32a, 32b is between about 0.200-0.250 millimeters, and the length 34L of the distal bevels 34a-b is between about 0.320-0.450 millimeters. In further example embodiments, the length 30L of the proximal bevel 30 is between about 0.810-0.880 millimeters, the length 32L of the intermediate bevels 32a, 32b is between about 0.229-0.236 millimeters, and the length 34L of the distal bevels 34a-b is between about 0.360-0.400 millimeters. In further example embodiments, the length 30L of the proximal bevel 30 is between about 0.600-1.050 millimeters, the length 32L of the intermediate bevels 32a, 32b is between about 0.110-0.350 millimeters, and the length 34L of the distal bevels 34a-b is between about 0.200-0.620 millimeters. In example embodiments, the length 30L1 of the proximal bevel 30 (measured between the peak and valley of the proximal bevel 30) is between about 0.350-0.390 millimeters. In further example embodiments, the length 30L1 is between about 0.355-0.383 millimeters. In further example embodiments, the length 30L1 is between about 0.325-0.400 millimeters. As such, in typical embodiments the multi-beveled point forms an elongated distal opening in communication with the lumen, the proximal bevel extends longitudinally from a proximal-most part of the multi-beveled point continuously along opposing elongated sides of the multi-beveled point, and the multi-beveled point has an overall axial length and the proximal bevel has an axial length that is at least half the overall axial length of the multi-beveled point.

The proximal, intermediate and distal bevels 30, 32a-b, 34a-b can also be defined by their respective arc lengths 30AL, 32AL, and 34AL, as shown in FIG. 8. The arc length is generally defined along the interior edges of the bevels, along the periphery 26 of the lumen 14, between the transitions between adjacent bevels. In one example form, the arc length 30AL of the proximal bevel 30 is between about 0.930-1.050 millimeters, the arc length 32AL of the intermediate bevels 32a-b is between about 0.220-0.255 millimeters, and the arc length 34AL of the distal bevels 34a-b is between about 0.175-0.245 millimeters. In another example form, the arc length 30AL of the proximal bevel 30 is between about 0.944-1.034 millimeters, the arc length 32AL of the intermediate bevels 32a-b is between about 0.232-0.240 millimeters, and the arc length 34AL of the distal bevels 34a-b is between about 0.203-0.213 millimeters. In another example form, the arc length 30AL of the proximal bevel 30 can be between about 0.650-1.550 millimeters, the arc length 32AL of the intermediate bevels 32a-b can be between about 0.150-0.350 millimeters, and the arc length 34AL of the distal bevels 34a-b can be between about 0.100-0.315 millimeters.

The pen needle 10 of the present invention can be formed from a steel material, for example a stainless steel, for example by drawing, molding or other manufacturing processes. In example forms, the needle 10 comprises an outer diameter OD and an inner diameter ID. The outer diameter OD is measured across the outer peripheral surface of the cannula 12 and the inner diameter ID is measured across the inner surface 15 of the lumen 14. In example forms, the outer diameter OD of the needle 10 is generally between about 0.1770-0.3460 millimeters, or for example from about 29 gauge to about 34 gauge, and the inner diameter is between about 0.0550-0.2260 millimeters. In further example forms, the outer diameter OD is between about 0.1778-0.3430 millimeters and the inner diameter ID is between about 0.0578-0.2230 millimeters. In further example forms, the outer diameter OD can be between about 0.1700-0.3500 millimeters and the inner diameter ID can be between about 0.0500-0.2300 millimeters. In example forms, the pen needle is about 4-25 millimeters in overall length. The chart below shows example dimensions of several gauge needles according to example embodiments of the present invention.

| Gauge | OD Nominal | Tolerance | OD Small | OD Large | Wall Thickness Minimum | Wall Thickness Regular | ID Small | ID Largest |
|---|---|---|---|---|---|---|---|---|
| 29 | 0.3366 | 0.0064 | 0.3302 | 0.3430 | 0.0600 | 0.0800 | 0.1702 | 0.2230 |
| 30 | 0.3112 | 0.0064 | 0.3048 | 0.3176 | 0.0600 | 0.0800 | 0.1448 | 0.1976 |
| 31 | 0.2604 | 0.0064 | 0.2540 | 0.2668 | 0.0600 | 0.0800 | 0.0940 | 0.1468 |
| 32 | 0.2350 | 0.0064 | 0.2286 | 0.2414 | 0.0500 | 0.0600 | 0.1086 | 0.1414 |
| 33 | 0.2096 | 0.0064 | 0.2032 | 0.2160 | 0.0500 | 0.0600 | 0.0832 | 0.1160 |
| 34 | 0.1842 | 0.0064 | 0.1778 | 0.1906 | 0.0500 | 0.0600 | 0.0578 | 0.0906 |

In example forms, the needle 10 of the present invention is generally manufactured in quantity, for example between about 50-1000 needles at a time in an automated process. Typically, an arm or other articulating structure comprises a system of fixtures for holding needle blanks, each of which is ground several times for form the needle tip resulting in the needle 10. In example forms, the bevels of the multi-beveled tip are ground by a disc-like grinding wheel or a belt. In example form, the arm holding the fixtures is positioned in close proximity to the grinder to allow for the grinder to provide the multi-beveled face on each of the needles sequentially or simultaneously. Preferably, the fixture system provides for rotation thereof such that the to-be needle can be rotated to form the distal bevels 34a-b. Adjustment to the inclination angle may be provided by angular movement of the arm and/or angular change of the inclination angle of each of the fixtures relative to the arm.

In example methods of manufacture, the end of a needle blank may start with a flat end face prior to being ground. The needle blank is then positioned at the inclination angle 30a relative to the longitudinal axis A and a grinder forms the proximal bevel 30. While remaining at the same angle of rotation, the inclination angle of the needle blank is changed to the inclination angle 32α relative to the longitudinal axis A. The grinder then forms the intermediate bevels 32a, 32b. The remaining distal bevels 34a-b are then formed, which requires adjustment to the inclination angle and the angle of rotation of the needle blank. In example form, the needle is adjusted to the inclination angle 34α and then rotated in the clockwise direction about ½ 34β, for example from the vertical axis B to the limit of 34β in the clockwise direction. The grinder then forms the first distal bevel 34a. The needle is then rotated the entire length of the rotation angle 34β in the counterclockwise direction and the grinder forms the second distal bevel 34b. Alternatively, the manufacturing process and/or the order of the steps to form the bevels can vary.

After the bevels are formed on the tip of the needle 10, the needle preferably goes through a bead blasting process whereby very small glass beads are projected onto the multi-beveled point such that any edges, intersections or transitions between bevels and adjacent surfaces are radiused, rounded, or otherwise smoothed. In one form, the projection of glass beads is not necessarily concentrated on a particular portion of the multi-beveled point 22, but instead generally projected at the point 22 in a direction generally perpendicular to the longitudinal axis A. In example forms, the spray of glass beads is controlled by the equipment and can be adjusted from a direction generally parallel to the extension of the needle 10 to a direction generally perpendicular to the extension of the needle 10 (including any angle therebetween). According to one example form, the angle of the spray of the glass beads is configured to be at about 30 degrees relative to the extension of the needle 10 (e.g., from being parallel therewith). The needle 10 then goes through an alkaline bath, an ultrasonic cleaning process, an acid bath, an electropolishing process, a cleaning process, and a passivation process. Preferably, these processes ensure that the needle is polished, smooth, free from burrs, and less resistant to corrosion. Optionally, after processing the needle (e.g., electropolishing, cleaning, and passivation), the needle undergoes a visual or machine inspection process to ensure that quality standards have been met. Generally, the inspection process comprises comparing the needle and its multi-beveled point against a sample or image of a satisfactory needle having targeted specifications. For example, in some example forms, the needle 10 is measured and the measurements are compared to a 2-dimensional dimensioned print of the needle. If the needle is within a specified range or tolerance of the target specifications, the needle passes the inspection and is assembled to form a pen needle, syringe or other item, and further treated and/or packaged for delivery.

FIGS. 9-14 show a pen needle 110 according to another example embodiment of the present invention. The pen needle 110 is in many aspects substantially similar to the pen needle 10 as described above, but comprises a three-bevel tip geometry rather than the five-bevel tip geometry described above. The pen needle 110 comprises a proximal bevel 130 and a pair of distal bevels 134a, 134b. Generally, the pen needle 110 comprises an elongate cannula 112 having a lumen 114 extending therethrough, which extends along a longitudinal axis A from a proximal end 116 to a distal end 120.

Figure 11:
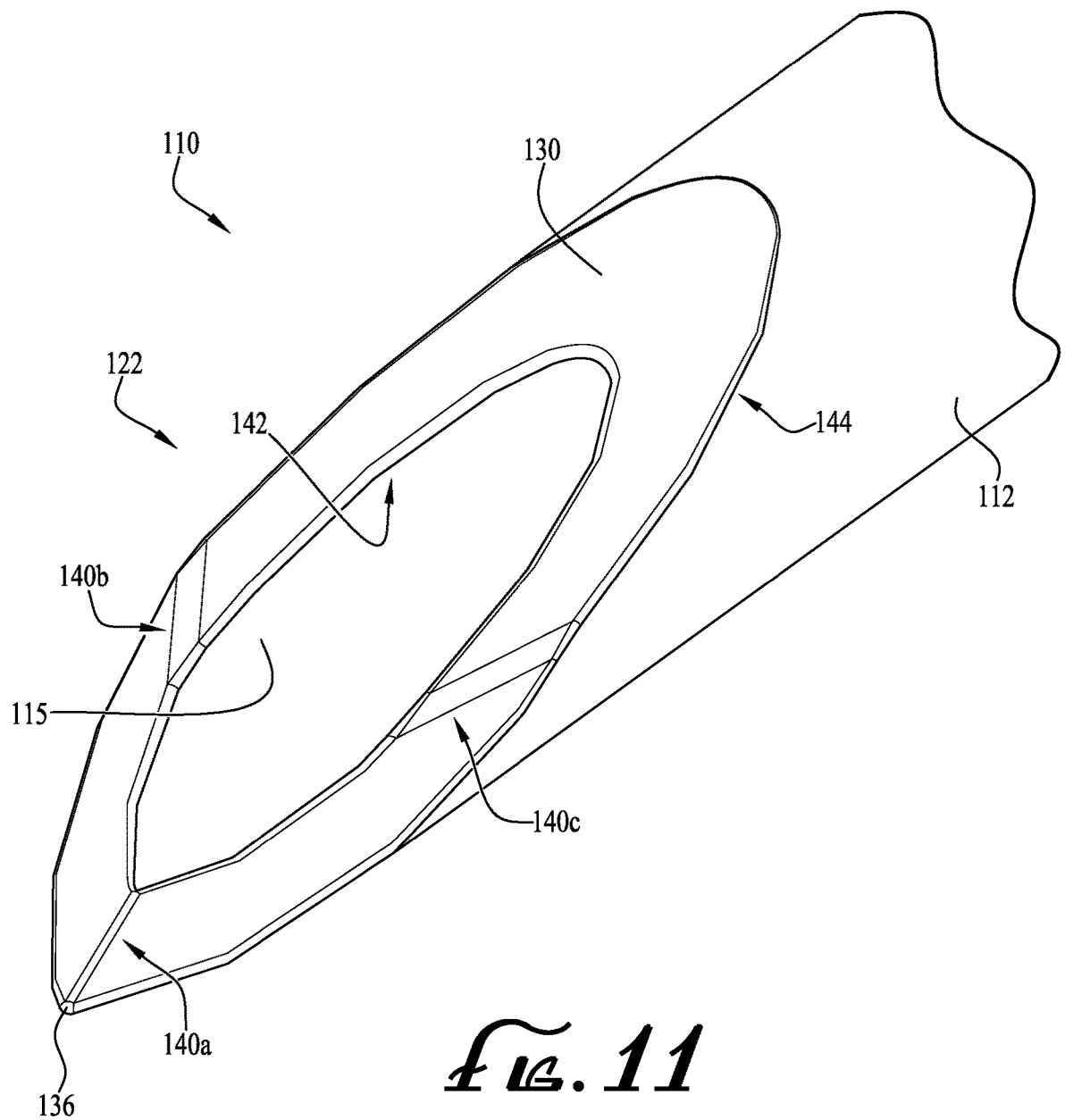
FIG. 11 is a detail view of the needle-tip portion of FIG. 9.
Figure 12:
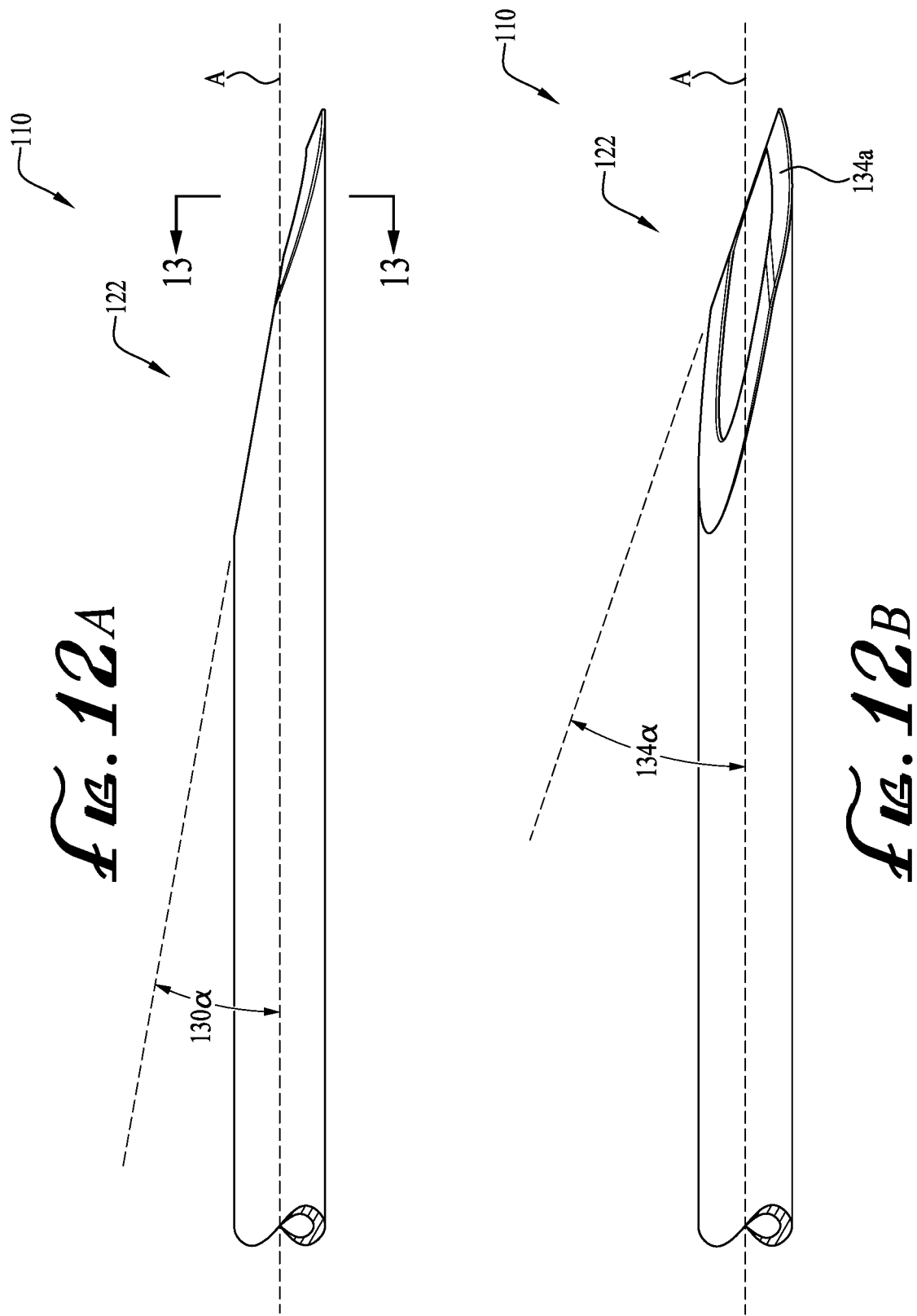
FIG. 12A is a side view of the needle-tip portion of FIG. 9, showing the inclination angle of the proximal bevel.
FIG. 12B is a side perspective view of the needle-tip portion of FIG. 12A, showing the inclination angle of the distal bevels.

A rounded, radiused, or otherwise smooth transition is optionally provided between the bevels, between the bevels and the lumen, and/or between the bevels and the outer periphery of the cannula 112. For example, as depicted in FIGS. 10-11, a first smooth transition 140a is provided between the distal bevels 134a, 134b, which meet together at a longitudinal apex 136. A second smooth transition 140b is provided between the distal bevel 134a and a portion of the proximal bevel 130, and a third smooth transition 140c is provided between the distal bevel 134b and a portion of the proximal bevel 130. A smooth transition 142 is also optionally provided between each of the bevels positioned along the periphery 126 of the lumen 114 and an interior surface 115 of the lumen 114 (e.g., bevel to intralumen transition), and a smooth transition 144 provided between the intersection of each of the bevels and the outer surface or periphery of the cannula 112.

Figure 13:
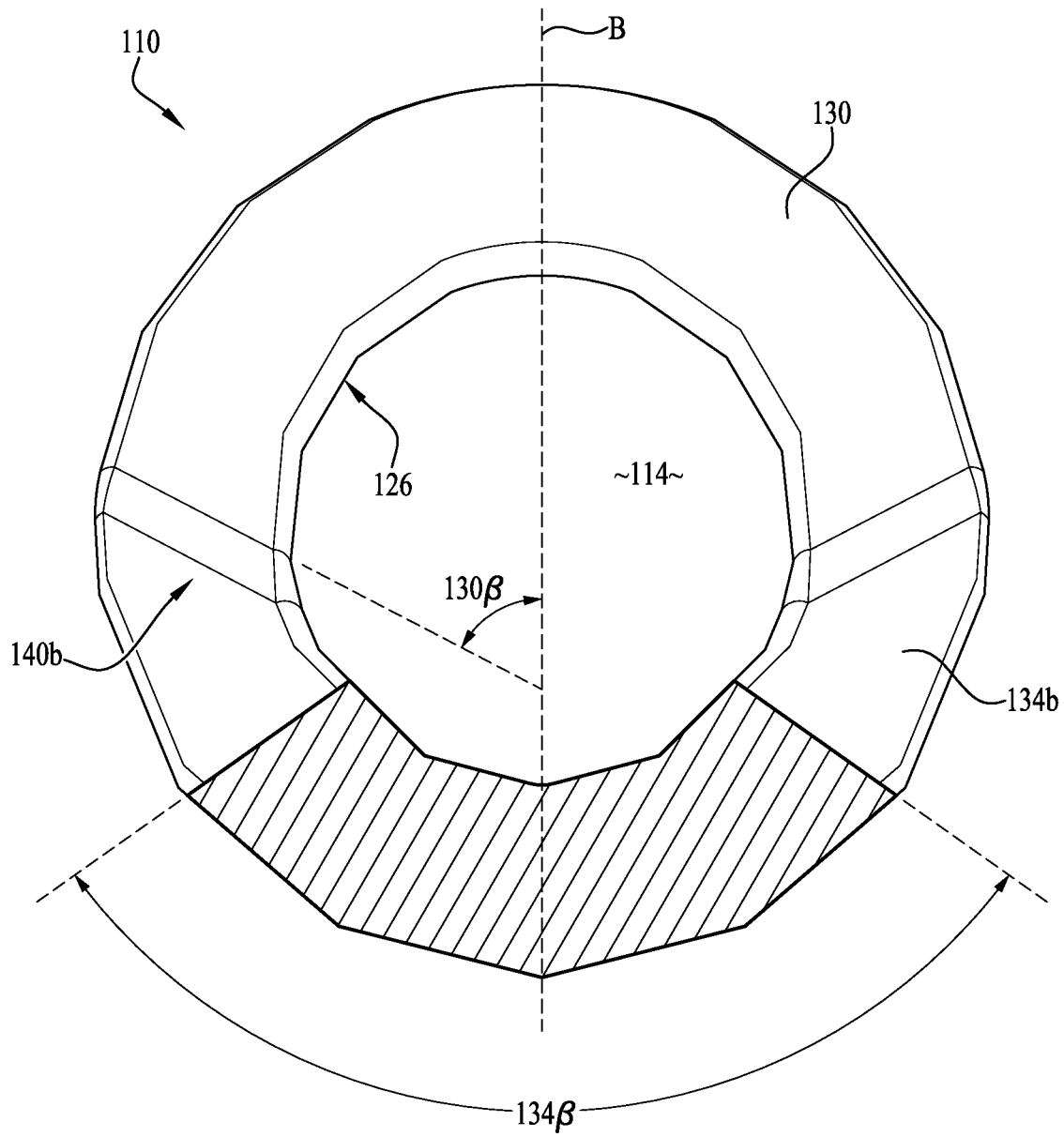
FIG. 13 is a partial cross-sectional view of the needle-tip portion of FIG. 12A taken along line 13-13, showing the angle of rotation of the distal bevels.
Figure 15A:
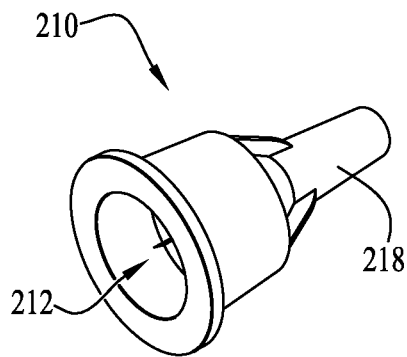
FIG. 15A is a distal-end perspective view of a pen needle according to another example embodiment of the present invention.
Figure 15B:
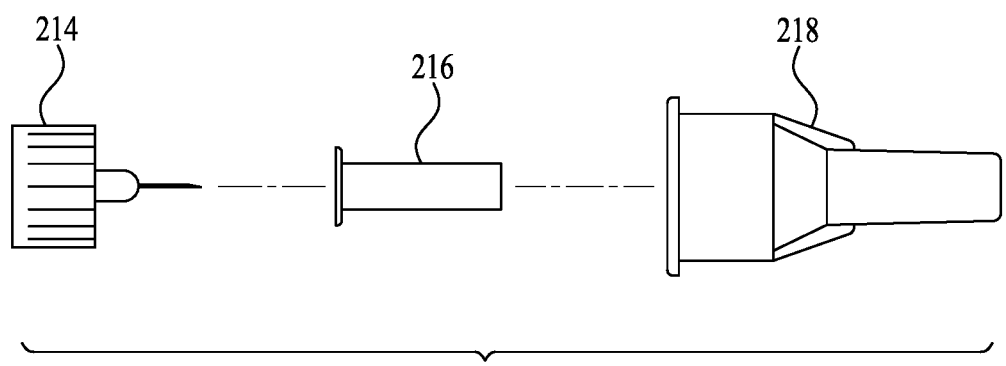
FIG. 15B is a perspective assembly view of the pen needle of FIG. 15A, shown with the protective caps or covers separated from the needle hub and with the sharp tip of the needle exposed.
Figure 19A:
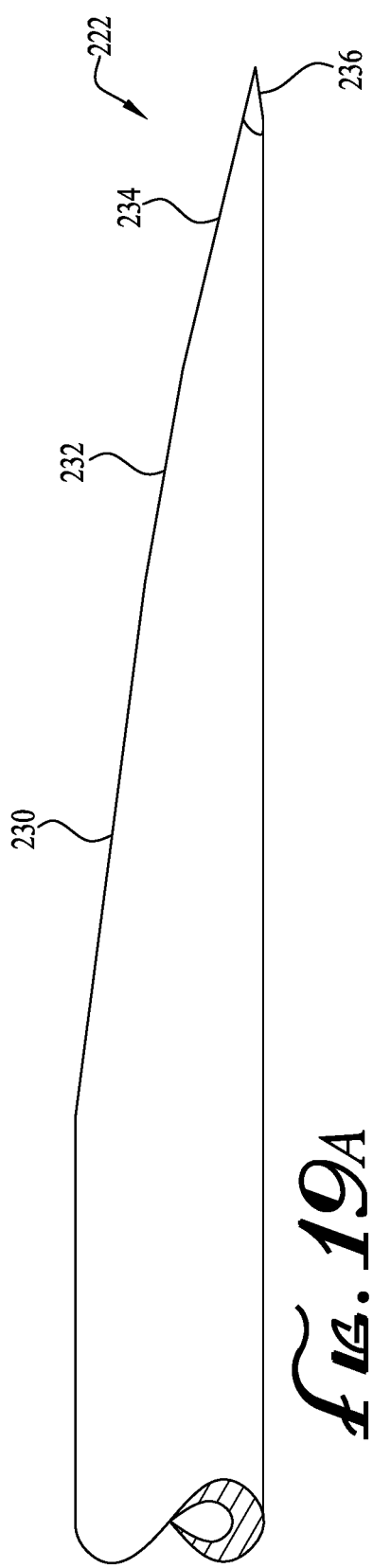
FIGS. 19A and 19B show detailed side and top views of another needle having a multi-bevel needle tip geometry according to an example embodiment of the invention.
Figure 19B:
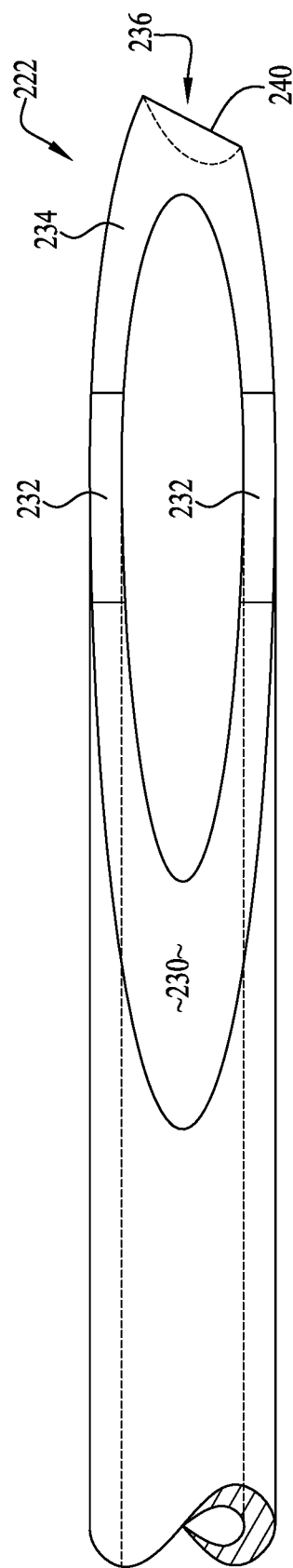
Figure 20:
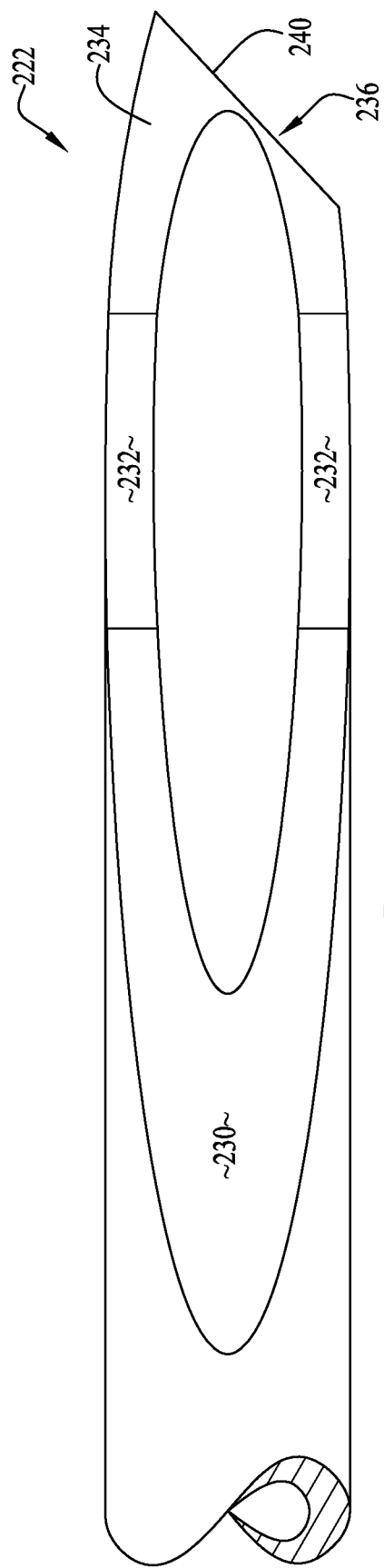
FIG. 20 shows a detailed top view of another needle having a multi-bevel needle tip geometry according to an example embodiment of the invention.

FIGS. 12A, 12B and 13 show greater details of the multi-bevel point 122. In the depicted embodiment of FIG. 12A, the proximal bevel 130 is formed at a first inclination angle 130a, defined relative to the longitudinal axis A. For example, in one example embodiment, the first inclination angle 130a is between about 7.3-7.7 degrees relative to the axis. In alternate embodiments, the first inclination angle 130a is between about 6.0-9.0 degrees. In the depicted embodiment of FIG. 12B, the distal bevels 134a, 134b are formed at a second inclination angle 134a relative to the longitudinal axis A, for example between about 18.0-19.0 degrees. In alternate embodiments, the second inclination angle 134a is between about 18.3-18.9 degrees. Optionally, the second inclination angle 134a is between about 17.0-20 degrees relative to the longitudinal axis A. Preferably, prior to forming the distal bevels 134a, 134b, the pen needle 110 is rotated about the longitudinal axis A in both the clockwise and counterclockwise directions respectively, such that the distal bevels 134a, 134b are formed at a substantially different rotational angle (and at a different inclination angle as described above) relative to the proximal bevel 130. As depicted in FIG. 13, the entire rotation of the needle 110 between the first distal bevel 134a and the second distal bevel 134b (shown as rotation angle 134β) is about 130 degrees relative to a vertical axis B. Thus, to form the first distal bevel 134a, the needle is rotated about the longitudinal axis A in the clockwise direction about 65 degrees and inclined at the inclination angle 134a. Similarly, to form the second distal bevel 134b, the needle 110 is rotated about the longitudinal axis A in the counterclockwise direction (from the 65 degrees clockwise position) about 130 degrees in the counterclockwise direction while remaining at the inclination angle 134α. Thus, in example forms, the rotational angle for forming the distal bevels 134a, 134b is generally provided by rotating the needle 110 about 65 degrees in both the clockwise and counterclockwise directions about the longitudinal axis A. Optionally, the rotational angle can be between about 55-75 degrees in the clockwise and counterclockwise directions.

As depicted, the smooth transitions between the bevels may be configured such that an angle 130β is defined between the vertical axis B and the smooth transitions 140b, 140c. In example forms, the angle 130β is about 73 degrees. Since the needle 110 is rotated in the clockwise and counterclockwise directions prior to forming the distal bevels 134a, 134b, the angle 130β will generally be between about 60 degrees to about 85 degrees relative to the vertical axis B.

As depicted in FIG. 14, in example embodiments, the length L of the multi-beveled surface 122 is between about 1.30-1.45 millimeters. In further example embodiments, the length L is between about 1.32-1.42 millimeters. In further embodiments, the length L can be between about 1.20-1.60 millimeters. In example embodiments, the length 130L of the proximal bevel 130 is between about 0.800-0.900 millimeters and the length 134L of the distal bevels 134a-b is between about 0.320-0.450 millimeters. In further example embodiments, the length 130L of the proximal bevel 30 is between about 0.810-0.880 millimeters and the length 134L of the distal bevels 34a-b is between about 0.360-0.400 millimeters. In further example embodiments, the length 130L of the proximal bevel 130 is between about 0.600-1.050 millimeters and the length 134L of the distal bevels 134a-b is between about 0.200-0.620 millimeters. In example embodiments, the length 130L1 of the proximal bevel 30 (measured between the peak and valley of the proximal bevel 130) is generally between about 0.350-0.390 millimeters. In further example embodiments, the length 130L1 is between about 0.355-0.383 millimeters. And in further example embodiments, the length 130L1 is between about 0.325-0.400 millimeters.

The proximal and distal bevels 130, 134a-b can also be defined by their respective arc lengths 130AL, 134AL. The arc length is generally defined along the interior edges of the bevels around the periphery 126 of the lumen 114, between transitions between the bevels. In one example form, the arc length 130AL of the proximal bevel 130 is between about 0.930-1.050 millimeters and the arc length 134AL of the distal bevels 134a-b is between about 0.175-0.245 millimeters. In example form, the arc length 130AL of the proximal bevel 130 is between about 0.944-1.034 millimeters and the arc length 134AL of the distal bevels 134a-b is between about 0.203-0.213 millimeters. In further example form the arc length 130AL of the proximal bevel 130 is between about 0.650-1.550 millimeters and the arc length 134AL of the distal bevels 134a-b is between about 0.100-0.315 millimeters.

In example embodiments, the outer diameter OD of the needle 110 is generally between about 0.1770-0.3460 millimeters, or for example between about 29 gauge to about 34 guage, and the inner diameter is between about 0.0550-0.2260 millimeters. In further example embodiments, the outer diameter OD is between about 0.1778-0.3430 millimeters and the inner diameter ID is between about 0.0578-0.2230 millimeters. In still further example embodiments, the outer diameter OD can be between about 0.1700-0.3500 millimeters and the inner diameter ID can be between about 0.0500-0.2300 millimeters. In example forms, the pen needle is about 4-25 millimeters in overall length. The chart above (see paragraph [0047]) shows example dimensions of several gauge needles according to example embodiments of the present invention.

FIGS. 15A-20 show additional features and embodiments of pen needles and needle tip geometries according to further example forms of the invention. In example forms, a pen needle 210 comprises a needle cannula 212 attached to a hub 214, a shield 216 and a container or cover 218. The needle 212 has a distal end 220 comprising a multi-beveled point 222. The multi-beveled point 222 comprises a plurality of beveled faces including a proximal bevel 230, a pair of intermediate bevels 232, one or more distal bevel(s) 234, and a back bevel 236. In example embodiments, the proximal bevel 230, intermediate bevels 232, and distal bevel 234 can be configured substantially similar to the respective bevels of the embodiments described above. In further example embodiments, one or more of the proximal bevel 230, the intermediate bevels 232, and the distal bevel(s) 234 are formed at different angles of inclination relative to one another and/or at rotational angles relative to one another.

The back bevel 236 is preferably formed on the rotationally opposite side or face of the needle cannula 212 (i.e., at a rotational orientation of about 180° about the axis C of the cannula) from the proximal bevel 230, intermediate bevels 232, and distal bevel 234. The back bevel 236 is preferably ground to a depth into the wall thickness of the cannula 212 sufficient to define a sharp leading edge 240 at the tip of the point 222 where the plane of the back bevel intersects the plane of the distal bevel 234, defining a chisel-tip geometry. Optionally, the back bevel 236 is formed at a slightly angularly offset (from 180°) rotational orientation relative to the distal bevel 234, to form an obliquely angled (relative to the axis C of the cannula) leading edge 240. In the embodiment depicted in FIG. 16c, the back bevel is ground at a rotational offset of about 152° from the distal bevel 234. In alternate embodiments, the rotational offset can be, for example, within a range of +/−45°, +/−30°, +/−15°, +/−5° and/or other offset from exactly 180°, to vary the angle of the leading edge 240 relative to the axis C of the cannula. Or alternatively, the back bevel 236 can be formed at a 180° rotational offset from the distal bevel 234 to form a leading edge perpendicular or transverse to the axis C of the cannula. The needle 210 can be formed in similar fashion as described above, in various different gauges, lengths, needle formats, etc., as well as various different bevel geometries and tip configurations, in example embodiments within the scope of the invention.

While the invention has been described with reference to preferred and example embodiments, it will be understood by those skilled in the art that a variety of modifications, additions and deletions are within the scope of the invention, as defined by the following claims.

What is claimed is:

1. A needle, comprising:
a cannula having a proximal end, a distal end, a longitudinal axis extending between the proximal and distal ends, an elongate lumen extending axially therethrough along the longitudinal axis, and a multi-beveled point at the distal end,
wherein the multi-beveled point includes a proximal bevel, a pair of intermediate bevels, and a pair of distal bevels, the proximal bevel being formed at a first angle of inclination relative to the longitudinal axis, the pair of intermediate bevels being formed at a second angle of inclination relative to the longitudinal axis, and the pair of distal bevels being formed at a third angle of inclination and having angles of rotation relative to a vertical axis which differ from one another, wherein the proximal bevel and the pair of intermediate bevels have a pair of transverse edges therebetween, and the pair of intermediate bevels and the pair of distal bevels have first and second smooth transition zones therebetween, and the pair of distal bevels have a third smooth transition zone therebetween, and
wherein the third smooth transition zone is rounded.

2. The needle of claim 1, wherein a difference of at least 1 degree is provided between the first and second angles of inclination.

3. The needle of claim 1, wherein a difference of at least 2 degrees is provided between the first and second angles of inclination.

4. The needle of claim 1, wherein an angular difference of at least 10% is provided between the first and second angles of inclination.

5. The needle of claim 1, wherein an angular difference of at least 20% is provided between the first and second angles of inclination.

6. The needle of claim 1, wherein the proximal bevel forms a continuous flat surface.

7. The needle of claim 6, wherein the multi-beveled point forms an elongated distal opening in communication with the lumen, and wherein the proximal bevel extends longitudinally from a proximal-most part of the multi-beveled point continuously along opposing elongated sides of the multi-beveled point.

8. The needle of claim 7, wherein the multi-beveled point has an overall axial length and the proximal bevel has an axial length that is at least half the overall axial length of the multi-beveled point.

9. The needle of claim 1, in combination with a hub to which the needle is affixed, forming a pen needle for replaceable use with an injector pen.

10. The pen needle of claim 9, in combination with the injector pen.

11. The needle of claim 1, wherein the third angle of inclination is about 17 to about 20 degrees relative to the vertical axis.

12. The needle of claim 1, wherein at least one smooth peripheral transition zone is formed between the proximal bevel, the pair of intermediate bevels, and the pair of distal bevels and an inner surface of the needle defining the lumen, between the proximal bevel, the pair of intermediate bevels, and the pair of distal bevels and an outer surface of the cannula, or both.

13. The needle of claim 1, further comprising a back bevel formed on a rotationally opposite side of the cannula from the distal bevels.

14. The needle of claim 13, wherein the back bevel is ground to a depth into a wall thickness of the cannula to define a chisel-tip geometry at a tip of the multi-beveled point.

* * * * *